United States Patent
White et al.

(10) Patent No.: US 9,964,476 B2
(45) Date of Patent: May 8, 2018

(54) SHEAR SENSOR ARRAY

(71) Applicant: TUFTS UNIVERSITY, Medford, MA (US)

(72) Inventors: Robert D. White, Medford, MA (US); Zhengxin Zhao, Medford, MA (US)

(73) Assignee: TUFTS UNIVERSITY, Medford, MD (US)

(*) Notice: Subject to any disclaimer, the term of this patent is extended or adjusted under 35 U.S.C. 154(b) by 0 days. days.

(21) Appl. No.: 14/522,653

(22) Filed: Oct. 24, 2014

(65) Prior Publication Data
US 2015/0114077 A1  Apr. 30, 2015

Related U.S. Application Data

(60) Provisional application No. 61/895,802, filed on Oct. 25, 2013.

(51) Int. Cl.
  *G01L 1/14* (2006.01)
  *G01M 9/06* (2006.01)
  *G01N 3/24* (2006.01)
  *G01L 15/00* (2006.01)

(52) U.S. Cl.
  CPC .............. *G01N 3/24* (2013.01); *G01L 1/146* (2013.01); *G01L 15/00* (2013.01); *G01M 9/065* (2013.01); *G01L 1/14* (2013.01)

(58) Field of Classification Search
  CPC . G01N 3/24; G01M 9/065; G01L 1/14; G01L 1/146
  See application file for complete search history.

(56) References Cited

U.S. PATENT DOCUMENTS

| | | | |
|---|---|---|---|
| 6,366,099 B1 | 4/2002 | Reddi et al. | |
| 8,104,346 B2 | 1/2012 | Horten et al. | |
| 2003/0199116 A1* | 10/2003 | Tai | G01M 9/065 438/53 |
| 2007/0116600 A1* | 5/2007 | Kochar | G01N 21/76 422/65 |
| 2008/0278029 A1* | 11/2008 | Pardo | C23C 18/32 310/307 |
| 2011/0138902 A1* | 6/2011 | White | H04R 1/406 73/147 |
| 2011/0314924 A1* | 12/2011 | Chandrasekharan | G01N 13/00 73/780 |
| 2014/0174204 A1* | 6/2014 | Chen | G01L 1/142 73/862.626 |

OTHER PUBLICATIONS

A. Padmanabhan, "Silicon micromachined sensors and sensor arrays for shear-stress measurements in aerodynamic flows", Feb. 1, 1997.*

(Continued)

*Primary Examiner* — R. A. Smith
*Assistant Examiner* — John M Royston
(74) *Attorney, Agent, or Firm* — Casimir Jones, S.C.

(57) ABSTRACT

The present disclosure relates to shear sensor arrays. In particular, the present disclosure relates to a floating element shear stress sensor array on a chip that is calibrated to high shear levels and is calibrated to determine the sensitivity to streamwise pressure gradients.

19 Claims, 8 Drawing Sheets

(56) References Cited

OTHER PUBLICATIONS

T. Pan, D. Hyman, M. Mehregany, E. Reshotko, B. Willis, "Calibration of microfabricated shear stress sensors", Jun. 29, 1995.*
Barlian et al., "Design and characterization of microfabricated piezoresistive floating element-based shear stress sensors" Sensors and Actuators A: Physical. 134 (2007) 77-87.
Brucker et al., "Feasability study of wall shear stress imaging using microstructured surfaces with flexible micropillars" Experiments in Fluids. 39 (2005) 464-474.
Chandrasekharan et al., "A metal-on-silicon differential capacitive shear stress sensor" (2009) 1537-1540.
Chandrasekharan et al., "A Microscale differential capacitive direct wall-shear-stress sensor" Microelectromechanical Systems, Journal of. 20 (2011) 622-635.
Chen et al., "Two-dimensional micromachined flow sensor array for fluid mechanics studies" Journal of Aerospace Engineering. 16 (2003) 85.
Dagamseh et al., ""Towards a high-resolution flow camera using artificial hair sensor arrays for flow pattern observations"" Bioinspiration & Biomimetics. 7 (2012) 046009.
Fernholz et al., "New developments and applications of skin-friction measuring techniques" Measurement Science and Technology. 7 (1996) 1396.
Ho et al., "Micro-electro-mechanical-systems (MEMS) and fluid flows" Annu. Rev. Fluid Mech. 30 (1998) 579-612.
Hyman et al., "Microfabricated shear stress sensors, Part 2: Testing and calibration" AIAA Journal. 37 (1999) 73-78.
Kalvesten et al., "An integrated pressure-flow sensor for correlation measurements in turbulent gas flows," Sensors and Actuators A 52:51-58, 1996.
Lofdahl et al., "MEMS-based pressure and shear stress sensors for turbulent flows," Meas. Sci. Technol., 10:665-686, 1999.
Lofdahl et al.,"Characteristics of a hot-wire microsensor for time-dependent wall shear stress measurements" Experiments in Fluids. 35 (2003) 240-251.
Naughton et al., "Modern developments in shear-stress measurement" Progress in Aerospace Sciences, vol. 38, Issues 6-7, Aug.-Oct. 2002, pp. 515-570.
Padmanabhan et al., "A silicon micromachined floating-element shear-stress sensors with optical position sensing by photodiodes" (1995) 436-9.
Padmanabhan et al., "A wafer-bonded floating-element shear stress microsensor with optical position sensing by photodiodes" Journal of Microelectromechanical Systems. 5 (1996) 307-315.
Padmanabhan et al., "Micromachined sensors for static and dynamic shear-stress measurements in aerodynamic flows" 1 (1997) 137-140.
Pan et al., "Microfabricated shear stress sensors, Part 1: Design and fabrication" AIAA Journal. 37 (1999) 66-72.
Patel et al., "Microfabricated Shear-Stress Sensors, Part 3: Reducing Calibration Uncertainty" AIAA Journal. 40 (2002) 1582-1588.
Savelsberg et al., "Calibration and use of a MEMS surface fence for wall shear stress measurements in turbulent flows" Exp. Fluids. 53 (2012) 489-498.
Schmidt et al., "Design and calibration of a microfabricated floating-element shear-stress sensor" Electron Devices, IEEE Transactions on. 35 (1988) 750-757.
Shajii et al., "microfabricated floating-element shear stress sensor using wafer-bonding technology" Microelectromechanical Systems, Journal of. 1 (1992) 89-94.
Sheplak et al., MEMS shear stress sensors: promise and progress, (2004). Table of Contents will suffice.
Tanner et al., "A Study of the Motion of Oil Films on Surfaces in Air Flow, with Application to the Measurement of Skin Friction", Journal of Physics E: Scientific Instrumentation, vol. 9, pp. 194-202, 1976.
Van Oudheusden et al., ""Silicon thermal flow sensors"" Sensors and Actuators A: Physical. 30 (1992) 5-26.
Von Papen et al., "A second generation MEMS surface fence sensor for high resolution wall shear stress measurement" Sensors and Actuators A: Physical. 113 (2004) 151-155.
Winter et al., "An outline of the techniques available for the measurement of skin friction in turbulent boundary layers" Prog. Aerospace Sci. 18 (1979) 1-57.
Zhe et al., "A microfabricated wall shear-stress sensor with capacitative sensing" Journal of Microelectromechanical Systems. 14 (2005) 167-175.
Zilliac et al., "Comparison of the Measured and Computed Skin Friction Distribution on the Common Research Model" Proceedings of the Aerospace Sciences Meeting, (2011). AIAA 2011-1129.

* cited by examiner $\tau_{yx}$: shear stress $\dfrac{\partial p}{\partial x}$: pressure gradient

SHEAR SENSOR ARRAY

CROSS REFERENCE TO RELATED APPLICATION

The present application claims priority to U.S. Provisional Patent Application Ser. No. 61/895,802 filed Oct. 25, 2013, the disclosure of which is herein incorporated by reference in its entirety.

FIELD OF THE INVENTION

The present disclosure relates to shear sensor arrays. In particular, the present disclosure relates to a floating element shear stress sensor array on a chip that is calibrated to high shear levels and is calibrated to determine the sensitivity to streamwise pressure gradients.

BACKGROUND OF THE INVENTION

The measurement of wall shear stress is important in many flow testing and device applications. Examples include drag measurements on air, space, land, and ocean-going vehicles both in test environments such as wind tunnels and in operation, as well as applications in active flow control. The measurement of surface shear stress is also important in industrial flow applications for fluid handling and manufacturing operations such as extrusion, and for biomedical devices in such applications as tissue engineering, where tissue development may depend on local shear stress. Flow regimes of interest may be as diverse as subsonic and supersonic turbulent boundary layers, turbulent pipe flows, and laminar flow in microchannels. Both steady and unsteady shear forces are of interest, and for some applications, particularly in turbulent boundary layer flows for aeroacoustic and structural acoustic applications, it may be important to capture the fluctuating shear stresses as well as the mean. Ideally, in order to capture the fine structure of turbulence, this would be done with a high spatial resolution on the order of 100 μm or smaller, and with high temporal resolution on the order of/ms or less (Sheplak, et al., (2004); Naughton et al., Prog. Aerospace Sci. 38 (2002) 515-570; Lofdahl et al., Measurement Science & Technology. 10 (1999) 665-686).

A number of techniques exist for measuring surface shear stress. These include oil film interferometry (Tanner, L. Blows, A study of the motion of oil films on surfaces in air flow, with application to the measurement of skin friction, Journal of Physics E: Scientific Instruments. 9 (1976) 194), heated patch or heated wire measurements (Van Oudheusden, Sensors and Actuators A: Physical. 30 (1992) 5-26; Lofdahl et al., Experiments in Fluids. 35 (2003) 240-251; Kalvesten et al., Sensors and Actuators A: Physical. 52 (1996) 51-58), hair-like sensors (Brucker et al., Experiments in Fluids. 39 (2005) 464-474; Dagamseh et al., Bioinspiration & Biomimetics. 7 (2012) 046009; Chen et al., Journal of Aerospace Engineering. 16 (2003) 85), surface fence measurements (Savelsberg et al., Exp. Fluids. 53 (2012) 489-498; von Papen et al., Sensors and Actuators A: Physical. 113 (2004) 151-155), and floating element techniques (see below). These techniques have been reviewed in a number of papers and have various advantages and disadvantages (Sheplak et al., supra; Naughton et al., supra; Winter, Prog. Aerospace Sci. 18 (1979) 1-57; Fernholz et al, Measurement Science and Technology. 7 (1996) 1396; Ho et al., Annu Rev. Fluid Mech. 30 (1998) 579-612).

Microelectromechanical system (MEMS) floating element sensors are one approach to the measurement of wall shear stress. In this measurement technology, a micromachined plate or shuttle is suspended using micromachined beam tethers. Under the influence of hydrodynamic forces, this "floating element" experiences a lateral deflection. The motion may be detected using capacitance change, piezoresistance, or optical methods. MEMS floating elements have the advantages of ease of use, high spatial and temporal resolution, and are a "direct" measurement technology insofar as they respond to momentum transfer at the wall. However, MEMS floating element sensors suffer from some drawbacks, including sensitivity to pressure gradients, potential for misalignment, and a possible lack of robustness to water or particle impingement (Sheplak et al., supra; Naughton et al., supra; Tanner et al., supra).

A number of authors have described these devices in the past. The earliest work on MEMS floating elements is that of Schmidt et al in 1988 (Schmidt et al., IEEE Transactions on. (1988) 750-757). Between 1995 and 1997, major contributions were made by Padmanabhan et al with the introduction of optical detection methods (Padmanabhan et al., The 8$^{th}$ International Conference on Solid State Sensors and Actuators and Eurosensors IX, IEEE (1995)436-439; Padmanabhan et al., Solid State Sensors and Actuators, International Conference on. Vol. 1. IEEE, (1997) 137-140; Padmanabhan et al., Journal of Microelectromechanical Systems. 5 (1996) 307-315). Using optical detection, a resolution of 1 mPa was reported, although most testing occurred at levels below 1 Pa. A single point was recorded by the research group demonstrating linearity to 10 Pa.

Pan et al, Hyman et al, and Patel et al used capacitive sensing for three different related designs that included on-chip electronics and force rebalancing (Hyman et al., AIAA Journal. 37 (1999) 73-78; Pan et al., AIAA Journal. 37 (1999) 66-72; Patel et al., AIAA Journal. 40 (2002) 1582-1588). Linear response was demonstrated out to 4 Pa for the first two designs. The third design is the largest maximum demonstrated linear response in the literature, maintaining linear response out to approximately 25-30 Pa of effective shear stress.

In more recent work, Zhe et al used differential capacitive measurements in a cantilever structure, and focused on high resolution at low stress levels (Zhe, et al., Journal of Microelectromechanical Systems. 14 (2005) 167-175), achieving 0.04 Pa resolution at stresses up to 0.2 Pa. Chandreskaran, et al also used differential capacitive measurement focusing on unsteady shear stress measurement (Chandrasekharan et al., (2009) 1537-1540; Chandrasekharan et al., Microelectromechanical Systems, Journal of. 20 (2011) 622-635), and were able to demonstrate 15 μPa/Hz$^{1/2}$ resolution at 1 kHz with linear response up to 2 Pa. Notable work by Barlian, et al (Barlian et al., Sensors and Actuators A: Physical. 134 (2007) 77-87) and Shajii, et al (Shajii et al., Microelectromechanical Systems, Journal of 1 (1992) 89-94.) describe piezoresistive floating elements for measurement in liquids.

The majority of MEMS sensors so far described in the literature for measurement in air have either not been calibrated, or not shown linear response, at shear stress levels above 4 Pa, yet average shear stresses on the order of 50 Pa or higher may be routinely encountered in typical air vehicle flow applications. For instance, at a free stream velocity of approximately 250 m/s (Mach 0.8), typical of commercial air liners, in air with sound speed 300 m/s, at a density of 0.4 kg/m3 and a viscosity of 1.5.10-5 Pa·s (approximate properties at a cruise altitude of 10 km), the Reynolds number is 7.106 m-1. The average shear stress under a zero pressure gradient flat plate incompressible turbulent boundary layer at 1 meter from the leading edge will be approximately 40 Pa (Cf=0.003), based on a ⅐th power law skin friction coefficient correlation (White, Viscous Fluid Flow 3rd Edition, McGraw-Hill Education, 2006), $$C_f = \frac{0.027}{Re_x^{1/7}} = \frac{\tau_w}{0.5\rho U^2} \quad (1)$$

where Cf is the skin friction coefficient, Rex is the Reynold's number based on distance down a float plate, $\tau_w$ is the wall shear stress, $\rho$ is the density of air and U is the free stream velocity. Compressibility effects at high subsonic Mach numbers will reduce the friction factor by approximately 10% (White, Viscous Fluid Flow 3rd Edition, McGraw-Hill Education, 2006), assuming there is not a great deal of heat transfer from the wall to the flow. These results are consistent with recent oil film measurements on a 2.7% scale model of a commercial airliner, the common research model, conducted in the NASA Ames 11 foot transonic tunnel under similar Mach and Reynold's number conditions to those experience in commercial flight. Measured values of Cf on the majority of the wing, tail, and body varied from approximately 0.002 to 0.004 (Zilliac et al., Proceedings of the Aerospace Sciences Meeting, (2011). AIAA 2011-1129).

Sensors with increased dynamic range, higher spatial resolution, and calibrated sensitivity to pressure gradients are needed.

SUMMARY OF THE INVENTION

The present disclosure relates to shear sensor arrays. In particular, the present disclosure relates to a floating element shear stress sensor array on a chip that is calibrated to high shear levels and is calibrated to determine the sensitivity to streamwise pressure gradients.

Accordingly, in some embodiments, the present disclosure provides a micromachined floating element array sensor, comprising: a solid support comprising at least one array of a plurality of floating shear sensors, wherein the shear sensors detect shear stress and determine the sensitivity of the sensors to pressure gradients. In some embodiments, each of the shear sensors comprises a movable center shuttle, a plurality (e.g., two) sets of variable capacitors, a plurality of surface bumps, and a series of folded beams. In some embodiments, the sensors are in an at least 1 (e.g., 2, 3, 4, 5, 6, 7, 8, 9, 10 or more) 4×4 arrays. In some embodiments, the array has a pitch of approximately 2 mm. In some embodiments, the solid support is approximately 1 cm². In some embodiments, the array comprises a plurality (e.g., 2, 3, 4, 5, 6, 7, 8, 9, 10 or more) of electroplated layers of metal (e.g., comprising copper and/or nickel). In some embodiments, the shear sensors further comprise a capacitance to digital converter.

In some embodiments, the present invention provides a system comprising a) any of the aforementioned sensors; and b) a computer process and user interface configured to measure shear stress using the sensor and report the shear stress using the user interface.

Additional embodiments provide a method of detecting shear stress, comprising: a) contacting any of the aforementioned sensors with a source of shear stress, and b) measuring said shear stress. In some embodiments, the method further comprises the step of measuring pressure gradient and correcting the shear stress value for the pressure gradient. In some embodiments, the shear stress is under a turbulent boundary layer.

Additional embodiments are described herein.

DEFINITIONS

As used herein, the term "shear stress" refers to the component of stress coplanar with a material surface interacting with a moving fluid (e.g., gas or liquid). Shear stress arises from the force vector component parallel to the surface.

As used herein, the terms "computer processor" and "central processing unit" or "CPU" are used interchangeably and refer to a device that is able to read a program from a computer memory (e.g., read only memory (ROM) or other computer memory) and perform a set of steps according to the program.

DETAILED DESCRIPTION

The present disclosure relates to shear sensor arrays. In particular, the present disclosure relates to a floating element shear stress sensor array on a chip that is calibrated to high shear levels and is calibrated to determine the sensitivity to streamwise pressure gradients.

Embodiments of the present disclosure provide arrays, systems, and methods for measuring shear stress in a variety of applications. The shear sensor arrays and systems described herein provide a high level of sensitivity that makes them useful in sensitive applications.

During the course of development of embodiments of the present disclosure resulted in the development of a floating element sensor array on a chip that has been calibrated to high shear levels, and also characterized to directly determine the sensitivity to streamwise pressure gradients. An exemplary sensor is described below, although one of skill in the art recognizes that modifications may be made. In some non-limiting examples, the sensor uses a differential capacitive sensing modality, and is configured mechanically in a folded beam floating element structure. The structure differs from previous devices in a number of ways. First, micromachined bumps are included on the sensor surface in an effort to increase sensitivity. Secondly, the chip includes 16 separately addressable sensors, which increases system robustness and opens the possibility of measurement of the spatial variation of shear with approximately 2 mm spatial resolution. Third, the sensor is fabricated in a low cost and easily implemented nickel on glass fabrication process that does not require deep etching or bonding steps. Finally, a direct capacitance to digital readout chip, the AD7747 (Analog Devices, Wilmington, Mass.), is used for high resolution differential measurement of capacitance that can be transmitted digitally over long distances with no concerns regarding shielding.

In order to assess the sensitivity of floating element sensors described herein to pressure gradients, sensors were tested in three laminar duct flow configurations, allowing separate experimental determination of the sensitivity to pressure gradient and shear stress. The pressure gradient sensitivity in these flow fields was found to be substantial, contributing approximately as much force on the structure as the surface shear.

Figure 1:
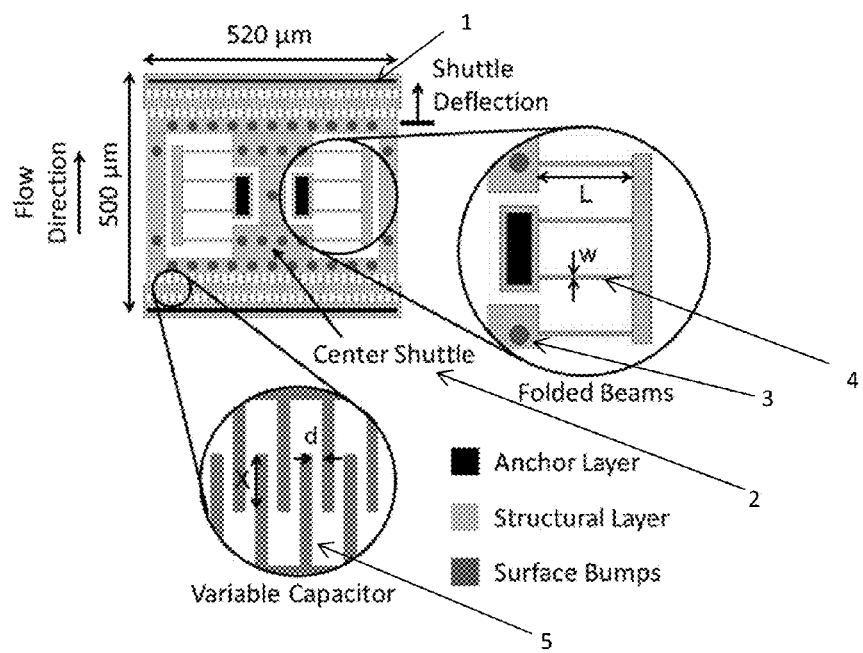
FIG. 1 shows a diagram of the mechanical structure of an exemplary floating element sensor.
Figure 3:
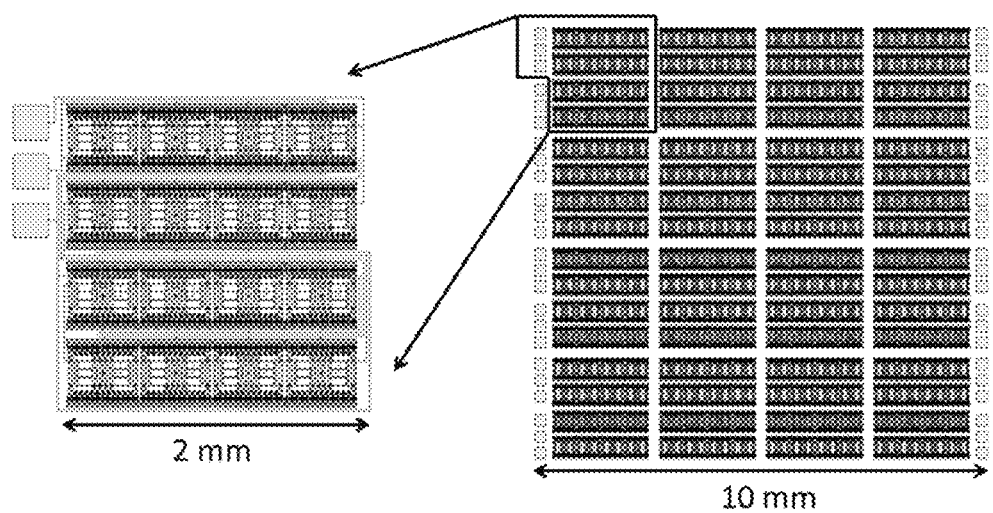
FIG. 3 shows the layout of the 1 cm² array chip. 256 elements are arranged into 16 groups of 16 elements. Each group is independently addressable.

Accordingly, embodiments of the present invention provide an array of floating shear sensors for use in a variety of applications. An exemplary sensor array is shown in FIG. 1. In some embodiments, the sensor comprises 1 or more (e.g., 1, 2, 3, 4, 5, 6, 7, 8, 9, 10 or more) arrays of sensor elements 1. In some embodiments, the arrays of elements 1 are arranged in a 4×4 pattern as shown in FIG. 3, although other arrangements are specifically contemplated (e.g., 2×2, 6×6, 8×8, and the like).

In some embodiments, each sensor is approximately 1-50 mm by 1-50 mm (e.g., 5-25 mm×5-25 mm or approximately 10 mm$^2$). In some embodiments, the solid support is 0.5-2.0 cm$^2$ (e.g., 1 cm$^2$). In some embodiments, the array has a pitch of approximately 0.5-5 mm (e.g., 2 mm).

Figure 5:
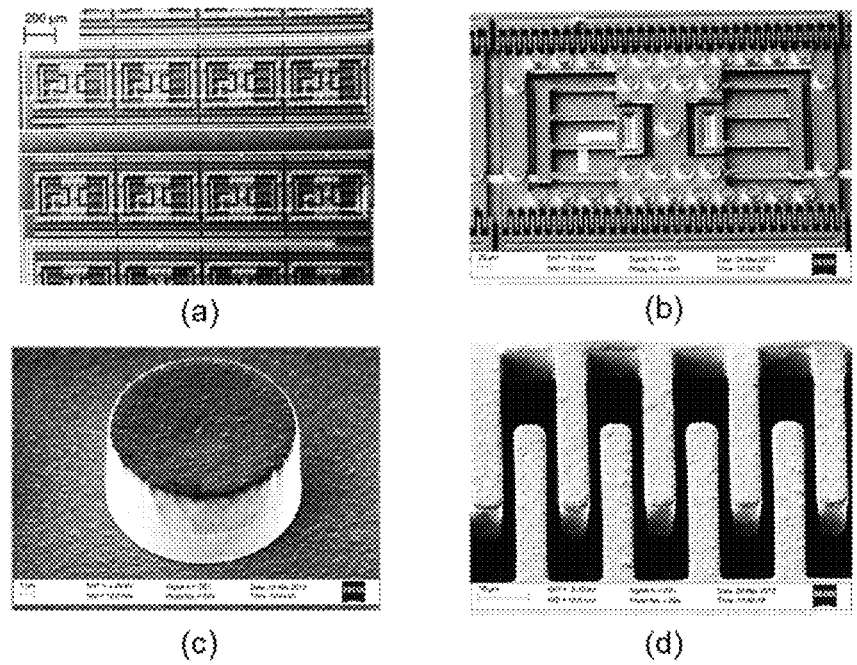
FIG. 5 shows SEM images of a released sensor chip. (a) Multiple elements in one group (b) A single element (c) A bump and (d) Variable capacitors (in this example, comb fingers).

Each sensor element 1 comprises a movable center shuttle 2 which experiences forces from interaction with the flow, one or more (e.g., two) sets of variable capacitors 5 for differential capacitive sensing of the motion of the shuttle, and a series (e.g., 2, 3, 4, 5, 6, 7, 8, 9, 10or more) of folded beams 4 to act as a spring support. In some embodiments, the folded beams 2 comprises a plurality of surface bumps 3 to increase sensitivity. In some embodiments, the inner beams and the outer fingers are fixed on the substrate through the anchors. The folded beam structure is employed to reduce the effects of residual stresses introduced during manufacturing. FIG. 5 shows SEM images of the sensor 1 chip array, sensor element 1, a surface bump 3, and variable capacitors (in this example, comb fingers) 5.

The central shuttle 2 can comprise any deflectable component attached to the substrate via anchors. The shape of the movable shuttle is not limited to a particular geometry or configuration. The configuration shown in FIG. 1 is exemplary.

The sensor further comprises a differential capacitance sensing component to sense capacitance of the motion of the shuttle. In some embodiments, the capacitance sensing component is a plurality of comb fingers, although other capacitive sensors can be utilized. Alternative capacitive sensors are commercially available (e.g., from Lion Precision, St. Paul, Minn.) and are described, for example, in U.S. Pat. Nos. 8,104,346 and 6,366,099; each of which is herein incorporated by reference in its entirety).

In some embodiments, the folded beams 4 comprise a plurality (e.g., 2, 4, 10, 20, 50, 100 or more per beam or other component) of surface bumps 3. The bumps can be of any geometry or size. In some embodiments, the bumps are cylindrical, although other shapes are contemplated. In some embodiments, bumps have a height of 1-50 µm (e.g., 5-25 µm, 8-15 µm, 10-12 µm, etc.) and a diameter of approximately 10-100 µm (e.g., 15-50 µm, 20-30 µm, etc.).

Figure 9:
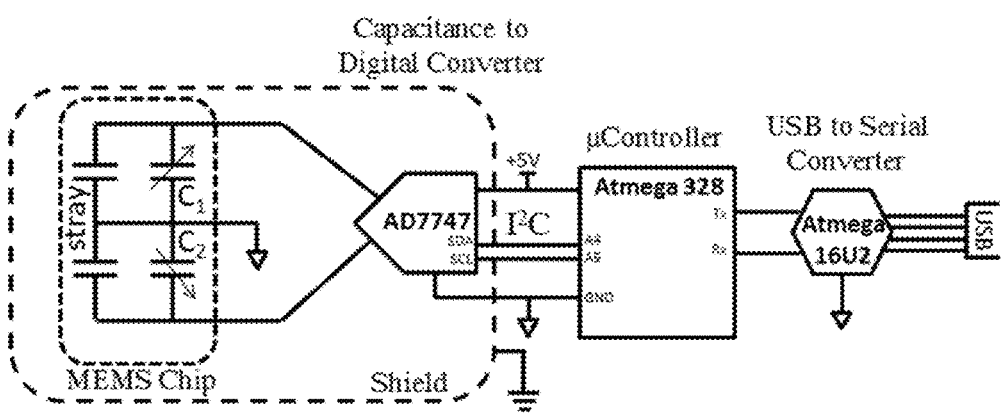
FIG. 9 shows readout electronics used an AD7747 capacitance to digital converter to perform differential capacitance measurements on the MEMS chip.

In some embodiments, the sensor further comprises a capacitance to digital converter to perform differential capacitance measurements. FIG. 9 shows the readout electronic for an exemplary commercially available capacitance to digital converter.

Figure 2:
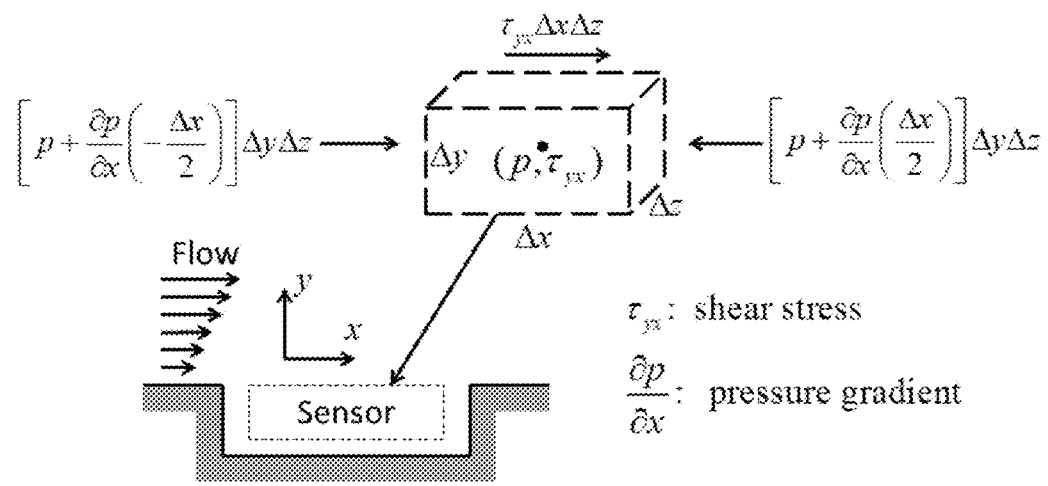
FIG. 2 shows a model of the flow interaction with the shear sensor including pressure gradient and surface shear.
Figure 12:
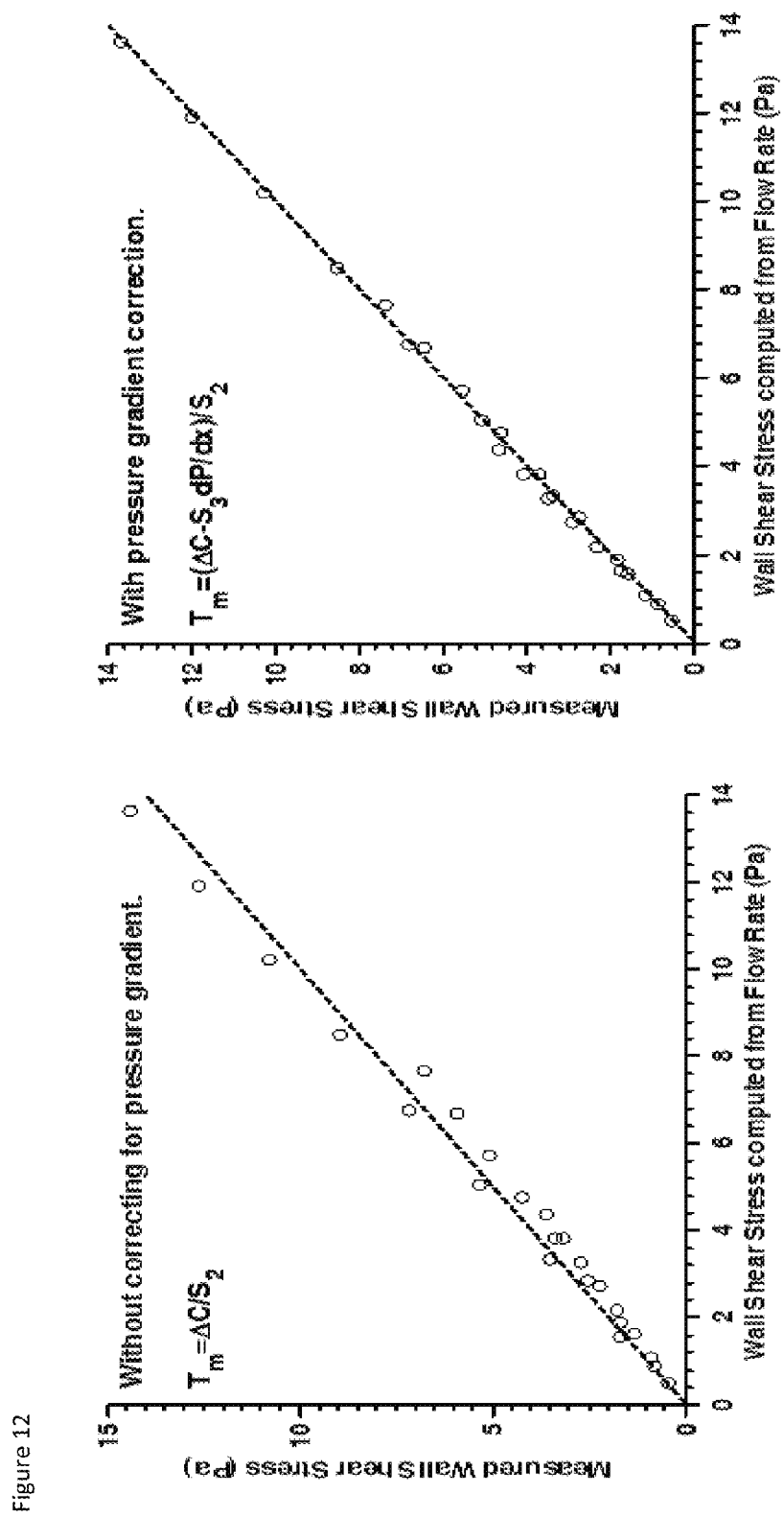
FIG. 12 shows a comparison of shear stress measured by the MEMS sensor (y-axis) to shear stress computed from the volume flow rate (x-axis). All 24 non-zero flow conditions are plotted as open circles. The dashed line is the unit line, indicative of an accurate measurement. The plot on the left assumes no pressure gradient sensitivity. The plot on the right corrects for the pressure gradient using the measured sensitivity as in equations (15) and (16).

In some embodiments, the sensor measures surface shear and pressure gradient as modeled in FIG. 2. Flow forces acting on the center shuttle bend the folded beams and create shuttle displacement primarily in the direction of the flow. The calibration of the sensor array to pressure gradients improves accuracy in measurement of shear stress. This is exemplified in FIG. 12.

Figure 4:
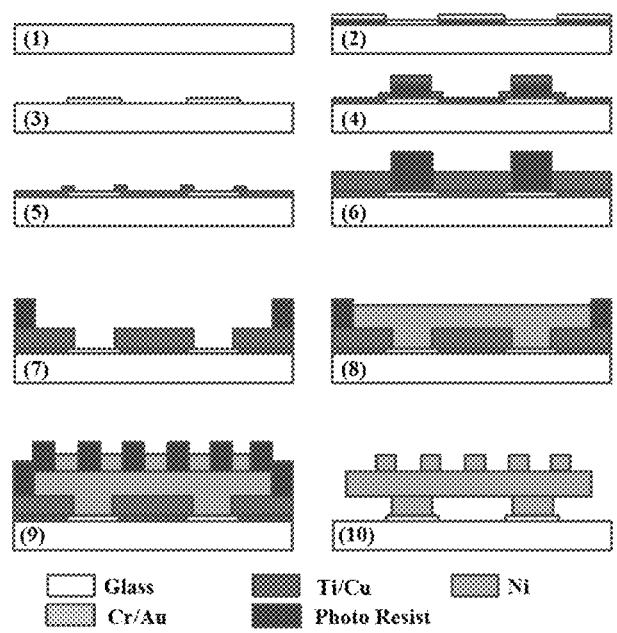
FIG. 4 shows nickel-on-glass fabrication process. Ti/Cu is used as a sacrificial layer.

The sensor elements and arrays of embodiments of the present disclosure are manufactured using any suitable method. In some embodiments, sensor elements are fabricated using micromachining. For example, in some embodiments, a substrate is fabricated by deposition of layers of metal (e.g., including but not limited to, Cr/Au and Ti/Cu). In some embodiments, a photoresist is lithographically patterned to create masks. An exemplary process is shown in FIG. 4, although other manufacturing methods are specifically contemplated.

The sensor arrays described herein find use in a variety of applications. Examples include, but are not limited to, measurement of shear stress (e.g., under a turbulent boundary layer) in the manufacturing, aeronautics, automotive, and the naval industries. For example, in some embodiments, the sensors arrays find use in the measurement of shear stress (e.g., skin friction) sensing for aerospace and automotive vehicles in ground testing to determine drag sources; shear stress (e.g., skin friction) sensing for aerospace vehicles in flight testing to determine drag sources; shear stress (e.g., skin friction) sensing for aerospace components (e.g., acoustic liners) in ground and flight testing to determine added drag from various liner designs; shear stress (e.g., skin friction) sensing during operation for separation detection and active (closed loop) flow control in manned and unmanned aerospace vehicles; shear stress sensing for studying aerodynamic forces on turbomachinery to improve efficiency and lifetime; shear stress sensing in wakes for studying coherent and incoherent structures shed by various bodies, including everything from civil structures to animal flight biomechanics; shear stress sensing in a variety of experimental studies used for the validation of computational fluid dynamics codes; and shear stress sensing in boundary layers to better understand aeroacoustic noise sources and propagation of aeroacoustics through shear layers.

In some embodiments, the present disclosure provides systems comprising the sensor arrays described herein and a computer system. In some embodiments, computer systems comprise a user interface operably connected to a computer processor in communication with computer memory. Computer memory can be used to store applications (e.g., data analysis applications).

The user interface can be used by a variety of users to perform different functions. In some embodiments, the user can access the interface by using any device connected to the computer system and/or sensor to provide and receive information.

EXPERIMENTAL

The following examples are provided in order to demonstrate and further illustrate certain preferred embodiments and aspects of the present invention and are not to be construed as limiting the scope thereof.

Example 1

Design
Electromechanical Modeling

The design of an exemplary floating element sensor is shown in FIG. 1. Each element has a movable center shuttle which experiences forces from interaction with the flow, two sets of comb finger for differential capacitive sensing of the motion of the shuttle, and a series of folded beam to act as a spring support. The four inner beams and the outer fingers are fixed on the substrate through the anchors. The folded beam structure is employed to reduce the effects of residual stresses introduced during manufacturing, as these stresses may relax out after structure release. The dimensions of the element are given in Table 1.

TABLE 1

As-manufactured dimensions of the floating element sensor.

| | |
|---|---|
| Finger gap, d (μm) | 2.88 |
| Finger width (μm) | 5.13 |
| Number of comb fingers on the shuttle, N | 64 |
| Thickness of structure, t (μm) | 8.8 |
| Width of folded beam, w (μm) | 5.13 |
| Length of folded beam, L (μm) | 99.2 |
| Height of bump (μm) | 11.7 |
| Diameter of bump (μm) | 24.7 |
| Height of air gap below shuttle (μm) | 5.2 |
| Shuttle top area, $A_m$ (mm$^2$) (includes finger and shuttle top surface area) | 0.085 |

Flow forces acting on the center shuttle bend the folded beams and create shuttle displacement primarily in the direction of the flow. Considering the shuttle and the fingers as a rigid body, the sensor stiffness in the lateral in-plane direction is easily related to the geometry of the beams (Pan et al., supra).

$$K_x = 2Et\left(\frac{w}{L}\right)^3, \quad (2)$$

where E is the Young's modulus of the structural material (Nickel), and w, t, and L are the width, thickness and length of each beam, as shown in FIG. 1. The aspect ratio (t to w) is designed to be high to minimize out-of-plane motion. Interdigitated overlap of the comb fingers determines the total active capacitance of the element, $$C = 2N\frac{\varepsilon t}{d}X, \quad (3)$$

where N is the number of fingers on the element, ε is permittivity of air, t is the thickness of the structure, d is the finger gap and X is the overlap length. This ignores capacitive fringing effects at the edges and assumes no out-of-plane motion. Thus, the differential change of capacitance for the element depends on the displacement δX only, $$\delta C = 2N\frac{\varepsilon t}{d}\delta X, \quad (4)$$

where δX is the displacement of the shuttle. The sensitivity, in terms of capacitance change, of the floating element to a constant applied force is thus $$S_1 = \frac{\partial C}{\partial F} = \frac{\partial C}{\partial X}\frac{\partial X}{\partial F} = \frac{\partial C}{\partial X}\frac{1}{K_x} = \frac{N\varepsilon L^3}{Edw^3}. \quad (5)$$

Fluid Forces

The structure responds to forces applied to the shuttle arising from interaction with the flow field. For a perfectly smooth shear sensor with no gaps or topology, the lateral force would simply be the surface area of the shuttle multiplied by the wall shear stress. Thus, some previous authors have assumed that the static force on the sensor would be $$F \approx A_m \cdot \tau_{yx} \quad (6),$$

where $A_m$ is the physical top surface area of the sensor shuttle and $\tau_{yx}$ is the wall shear stress present at the wall. However, for a sensor that includes gaps, topology, roughness, and packaging topology, it is expected that the steady fluidic force depend on both the time average local wall shear stress, the local streamwise pressure gradient in the flow, and the details of the geometry at the microscale. It is also possible that the compressibility of the flow (Mach number) plays a role, and, in the case of boundary layer flows, the boundary layer thickness may be important.

To build a flow interaction model, the sensor is considered to have an effective rectangular shape, and to be acted on by the local surface shear stress and the pressure gradient present in the flow, as diagrammed in FIG. 2.

It is emphasized that the effective size of the element, Δx by Δy by Δz, is not identical to the physical size of the element. These effective dimensions are determined experimentally, and to first order account for the unknown details of the microscale flow around the element. They can also account for small manufacturing nonuniformities or imperfect packaging, such as a slightly misaligned sensor. It is likely that these dimensions will be of the same order of magnitude as the physical size of the element, but certainly are not expected to be identical to its physical size. Given this model, the fluidic force acting on the element is $$F = \tau_{yx} \cdot \Delta x \Delta z - \left(\frac{\partial p}{\partial x}\right) \cdot \Delta x \cdot (\Delta y \Delta z). \quad (7)$$

By combining equations (5) and (7), the differential sensitivity of a single element to the two flow variables can then be written $$S_2 = \frac{\partial C}{\partial \tau_{yx}} = \frac{\partial C}{\partial F} \frac{\partial F}{\partial \tau_{yx}} = \frac{N\varepsilon L^3}{Edw^3} \Delta x \Delta z \quad (8)$$

$$S_3 = \frac{\partial C}{\partial (\partial p / \partial x)} = \frac{\partial C}{\partial F} \frac{\partial F}{\partial (\partial p / \partial x)} = \frac{-N\varepsilon L^3}{Edw^3} \Delta x \Delta y \Delta z, \quad (9)$$

where $S_2$ is the sensitivity to shear, and S3 is the sensitivity to pressure gradient.

In order to increase the sensitivity of the sensor by increasing the effective area of interaction with the flow ($\Delta x$, $\Delta y$, and $\Delta z$), surface bumps were fabricated on the top of the shuttle. As shown in FIG. 1, 35 cylindrical bumps, each 12 μm high with a diameter of 25 μm, were fabricated in a distributed pattern.

Array

In order to measure local spatial variation in unsteady shear, the 1 cm square chip was designed to include an array of 16 by 16 elements. The 256 elements were subdivided into 16 groups of 16 elements each, so that each group has a 4 by 4 pattern of elements as shown in FIG. 3. Each group has independent connections routed to three electrical pads for the top combs, bottom combs, and common (center shuttle) electrodes. The groups are approximately 2 mm×2 mm in size, thus the spatial resolution for shear measurements of the array-on-a-chip is on the order of 2 mm. The local shear stress of a group or average shear of the whole chip can be measured separately. This allows the end user to trade-off between spatial resolution and sensitivity. In addition, a major benefit of the array architecture is that failure of a single element or single group, either during fabrication or during operation, does not destroy the functionality of the entire chip. This is a desirable feature for sensors deployed in harsh operating environments where single elements can be lost to particulates or moisture, but the chip continues to function, albeit with reduced sensitivity.

Fabrication and Packaging

The sensors were fabricated using a four-mask nickel surface micromachining process in the Tufts Micro/Nano Fab, shown in FIG. 4. The process starts with a soda lime glass substrate of 550 μm thickness. Steps 1 to 5 in FIG. 4 show 75 nm/250 nm thick Cr/Au interconnects, followed by another thin seed layer of Ti/Cu (30 nm/300 nm). Both layers were sputter deposited and patterned by liftoff using a two layer Liftoff resist, LOR-20B (Microchem, Newton, Mass.). The LOR uses a two layer process to create a reentrant photoresist profile. This is very effective at preventing the side wall of the resist being coated in the deposition step and creating either raised ridges at the edges of patterns or metal particles. Next, a photoresist layer was photolithographically patterned to form anchor regions to the substrate and an oxygen plasma descum performed. A 5 μm sacrificial layer of copper was then electroplated on top of the seed layer to cover the entire substrate except the anchor regions, as shown in step 6. Plating was done using a commercial copper sulfate plating solution (Technic Inc, Cranston, R.I.) at room temperature. Care was taken to minimize the surface roughness by controlling the plating current and brightener percentage as well as agitating and continuously filtering the plating solution. For a plating current density of 5 mA/cm2 and a total 5 um thickness of copper, the RMS surface roughness is between 50 nm and 150 nm.

Subsequently, a 9 μm height floating element layer and a 12 μm height bump layer were electroplated in two steps using a commercial Nickel Sulfamate (Technic Inc, Cranston, R.I.) plating solution. The patterns were established using a thick photoresist and descumed in an oxygen plasma. A brief acid etch was conducted to remove any copper oxide, and then Nickel was plated at 50° C. at 5 mA/cm2 with a deposition rate of approximately 100 nm/min. The surface roughness of the nickel after plating is 150 nm to 200 nm. The roughness appears to be a reflection primarily of the roughness of the Cu sacrificial layer.

Finally, a protective photoresist layer was spun on for dicing. After dicing, the sacrificial copper layer was etched away in a mixture of 1 part Acetic Acid to 1 part 30% Hydrogen Peroxide to 18 parts DI water for 24 hours. The chip was rinsed in water, Isopropanol, and Methanol, and allowed to air dry in a dry box that has been flooded with clean dry air with a low relative humidity. SEM images in FIG. 5 show the released structure. The as manufactured dimensions shown in Table 1 were taken from the SEM images for in-plane dimensions and from white light interferometry measurements for layer thicknesses.

Figure 6:
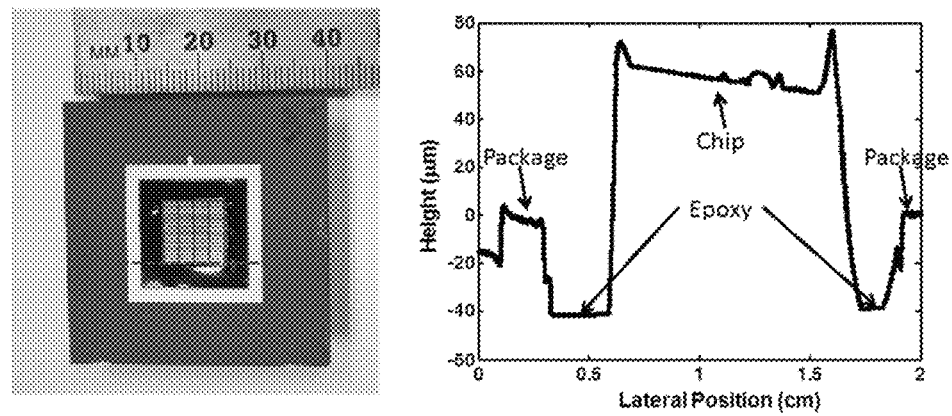
FIG. 6 shows (Left) A finished sensor chip packaged and potted in a ceramic pin grid array package. A dashed line indicates the line along which a stylus profilometer scan was taken. (Right) The measured height of the surface topology along the indicated scan line.

After releasing, the sensors were packaged into a 4 cm by 4 cm ceramic pin grid array hybrid package (CPGA). First, the CPGA cavity is partially filled with potting epoxy (Namics Chipcoat G8345-6) which is cured. The epoxy is then CNC milled to the appropriate height, including a small square pocket to center and align the chip. The chip is mounted into the pocket with a thin epoxy film. The package is ball bonded to the chip using 25 micrometer diameter gold wire. Finally, the wirebonds are potted in epoxy, which is allowed to settle and cure, with multiple layers being applied until a flat surface is achieved around the chip and package. Using this method, it is possible to create a flat surface with a total maximum topology from the ceramic surface, onto the epoxy, over the wirebonds and onto the chip of approximately 100 micrometers. FIG. 6 shows a photograph of the packaged chip, and a stylus profilometer scan of the surface topology from the package, onto the epoxy, across the wirebonds, onto the chip and back onto the package. As can be seen, the packaging exhibits approximately 0.1 mm of total topology, and the chip is parallel to the package surface within 0.1°.

Experimental Methodology

Flowcell

Figure 7:
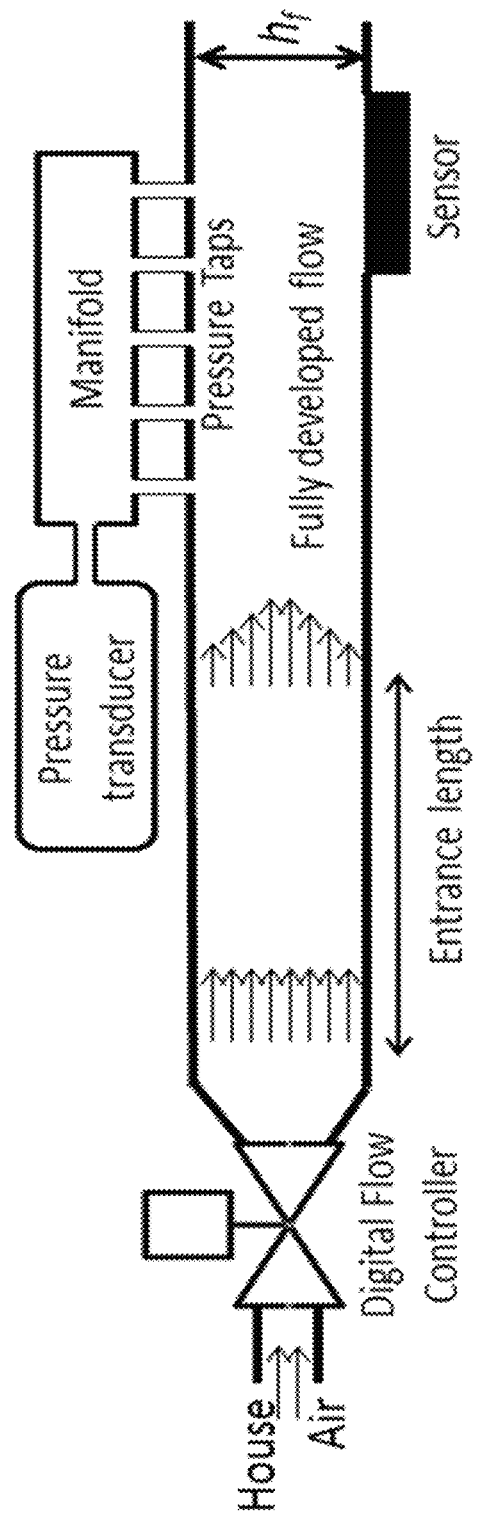
FIG. 7 shows a diagram of a laminar flow cell test apparatus.

The floating element sensor was tested in a laminar flowcell, similar to that described previously (Hyman et al., supra). A duct flow channel was created by CNC milling a thin rectangular slot into an aluminum plate, and assembling this with a flat bottom plate with a square cutout for flush mounting the package. The slot is 28 mm wide. Three different height slots were used, $h_3 2$ 0.30, 0.40 and 0.53 mm. The inlet air supply is house clean dry air, and is regulated via computer control using a digital flow controller, Omega FMA3812 (Omega Engineering, Stamford, Conn.). This unit controls the total volume flow rate from 0 to 40 cubic feet per hour (CFH). The outlet flow exits to atmosphere. FIG. 7 is a diagram of test setup. Five static pressure taps are included on the top of the channel, with a pitch of 12.7 mm, along the streamline to measure the pressure gradient in the fully developed range. The fifth pressure tap is located directly above the sensor. The static pressure is measured using an Omega PX209 pressure transducer (Omega Engineering, Stamford, Conn.). Care was taken to ensure that the flow cell is long enough that the flow is fully developed before reaching the pressure taps or the device under test. For flow rates of 40 CFH or less, the flow in the duct is laminar, and the flow profile will follow the Poiseuille flow profile for a narrow slot (White, Viscous Fluid Flow 3rd Edition, McGraw-Hill Education, 2006), $$u(y) = \frac{6Q}{b_f h_f}\left(\frac{1}{4} - \left(\frac{y}{h_f}\right)^2\right) \quad (10)$$

where Q is the volume flow rate, $b_f$=28 mm is the duct width, $h_f$=0.3, 0.4 or 0.5 mm is the duct height, and y=$-h_f/2 \ldots h_f/2$ is the coordinate. At Q=$3.15 \cdot 10^{-4}$ m$^3$/s (40 CFH), for the smallest duct, the centerline velocity is 56 m/s, resulting in a centerline Mach number of 0.16 and an area averaged Mach number of 0.11. Hence, even at the highest flow rates, the flow can be considered incompressible.

The Reynold's number based on the average flow velocity and hydraulic diameter is $$Re_{D_h} = \frac{2\bar{u}\rho h_f}{\mu} = \frac{2Q\rho}{b_f \mu}, \quad (11)$$

which does not vary with duct height. At the maximum flow rate of Q=$3.15 \cdot 10^{-4}$ m$^3$/s (40 CFH), using $b_f$=28 mm, g=$1.8 \cdot 10^{-5}$ Pa·s, and ρ=1.2 kg/m3, =1500 (White, Viscous Fluid Flow 3rd Edition, McGraw-Hill Education, 2006). Transition to turbulence in parallel plate flow occurs above a Reynolds number of 2000 (White, Viscous Fluid Flow 3rd Edition, McGraw-Hill Education, 2006), thus the flow is expected to remain laminar, for all duct heights, up to the highest flow rate tested. Given this, the pressure gradient and wall shear stress are expected to be $$\frac{\partial p}{\partial x} = \frac{-12\mu Q}{h_f^3 b_f} \quad (12)$$

and $$\tau_{yx} = \frac{-1}{2}h_f\left(\frac{dp}{dx}\right) = \frac{6\mu Q}{h_f^2 b_f}. \quad (13)$$

Figure 8:
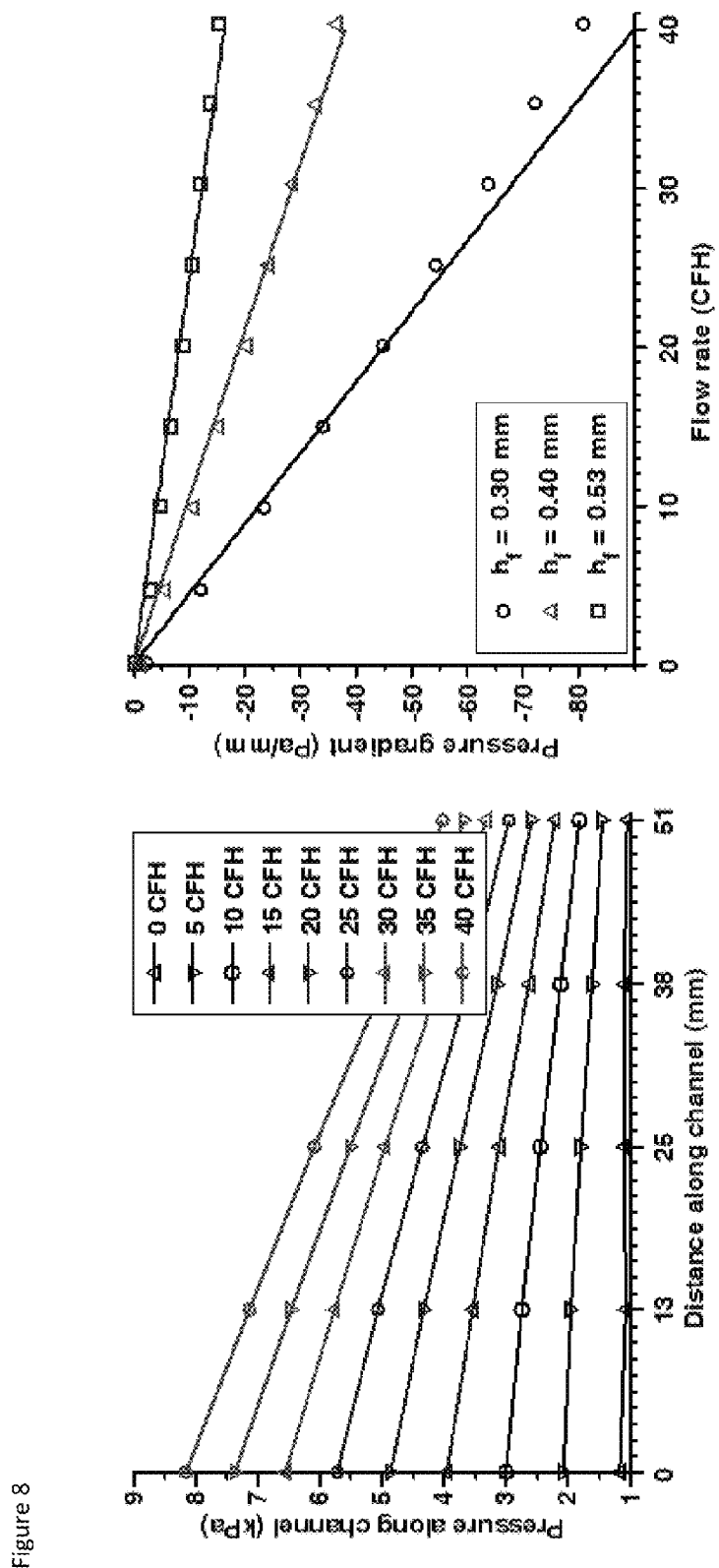
FIG. 8 shows (Left) Measured pressure as a function of distance down the duct for different flow rates in a 0.30 mm high duct. (Right) Measured pressure gradient as a function of flow rate (symbols) compared to the Poiseuille flow model (lines), equation, plotted for the three duct heights.

Since pressure gradient and shear stress scale as $h_f^{-3}$ and $h_f^{-2}$ respectively, it is possible to produce laminar flow regimes with linearly independent values of the two fluid forcing terms by varying the duct height. The measured pressure gradient is shown in FIG. 8, and exhibits excellent agreement with the expectations of equation (12), giving considerable confidence that the flow is fully developed and laminar, and that the shear stress of equation (13) is accurate.

Electronics

A schematic of the system electronics is shown in FIG. 9. An AD7747 (Analog Devices, Wilmington, Mass.) capacitance to digital converter chip is used to measure the differential capacitance between the top and bottom electrodes on the MEMS chip. The chip uses an AC excitation and a sigma delta modulator to measure differential capacitance changes of ±8 pF, and is capable of removing offset static differential capacitances as high as 17 pF. On chip registers control the conversion rate, AC excitation level, and allow for nulling of any static capacitance offset. The best results in terms of noise performance can be achieved using the slowest conversion rate of 219.3 ms, and an excitation voltage level of ±⅜×VDD, which is a voltage swing from 0.625 V to 4.375 V applied to the MEMS capacitors. With these settings the AD7747 is expected to provide a resolution of 9.0 aF/√Hz (Analog Devices, 24-Bit Capacitance to Digital Converter with Temperature Sensor, Datasheet Rev 0 (2007)).

Analog to digital conversion happens at the AD7747, which is located as close as possible to the MEMS chip and enclosed in a grounded shield. This helps to reduce electromagnetic interference (EMI). Once conversion happens, the signal is now digital and immune to EMI. The AD7747 communicates with an Atmega328 microcontroller using the two wire I2C protocol. The microcontroller then communicates with a computer over USB via an Atmega16U2 configured as a serial to USB converter. The speed of the system is limited by the conversion time of the AD7747. Shorter conversion times down to 22 ms can be used, but result in a lower capacitance resolution.

Results

Figure 10:
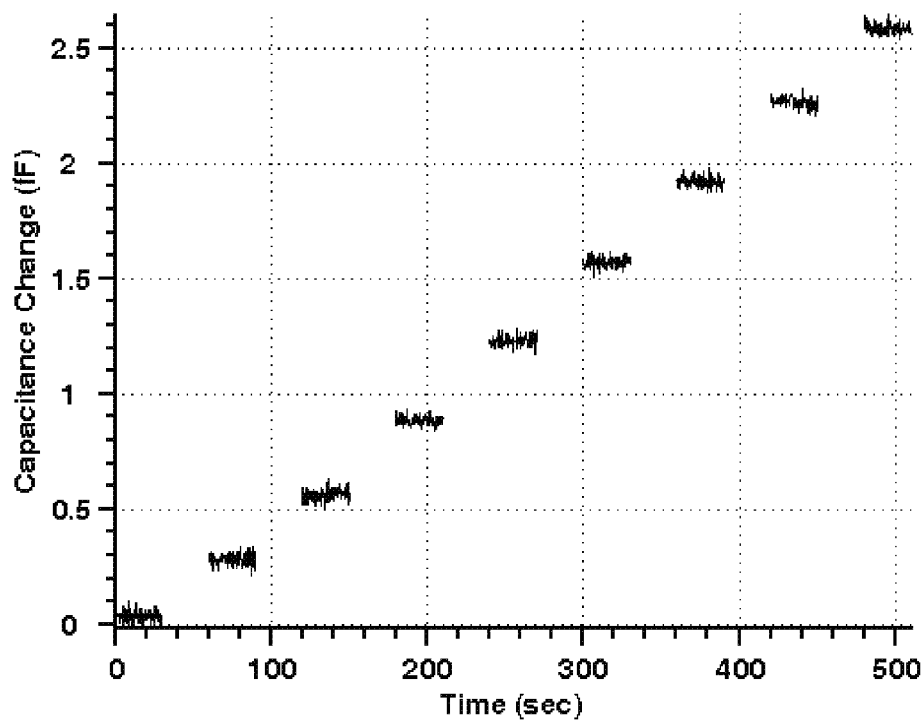
FIG. 10 shows measurement of the change in capacitance of 8 groups on the MEMS chip during flow testing in the 0.30 mm high flow duct. Each step in capacitance corresponds to a 5 CFH increase in flow rate, from 0 to 40 CFH.

The packaged sensor chip was tested in the laminar flow cell at each of the three duct heights. For the tests presented here, 8 of the 16 groups on the chip were connected in parallel, so the output is the total capacitance change from 128 elements. Before each test, the electronics were turned on for 2 hours with no flow, and then the flow was turned on at 10 CFH for an additional two hours. This conditioning was found to remove startup transients that were otherwise observed. After the 4 hour turn on and soak, the flow rate was controlled by the computer via the digital flow controller starting at 0 flow rate, and increasing to 40 CFH in steps of 5 CFH. Each flow rate was held for 60 seconds. The first 30 seconds at each condition were not integrated, to allow the flow and sensor to settle. The differential capacitance measured during the second 30 seconds was used for computing the average and standard deviation of the capacitance change at that flow rate. As mentioned previously, a conversion rate of 219.3 ms was used on the AD7747. Additional communications overhead resulted in 2.94 capacitance samples per second. A typical result is shown in FIG. 10.

Figure 11:
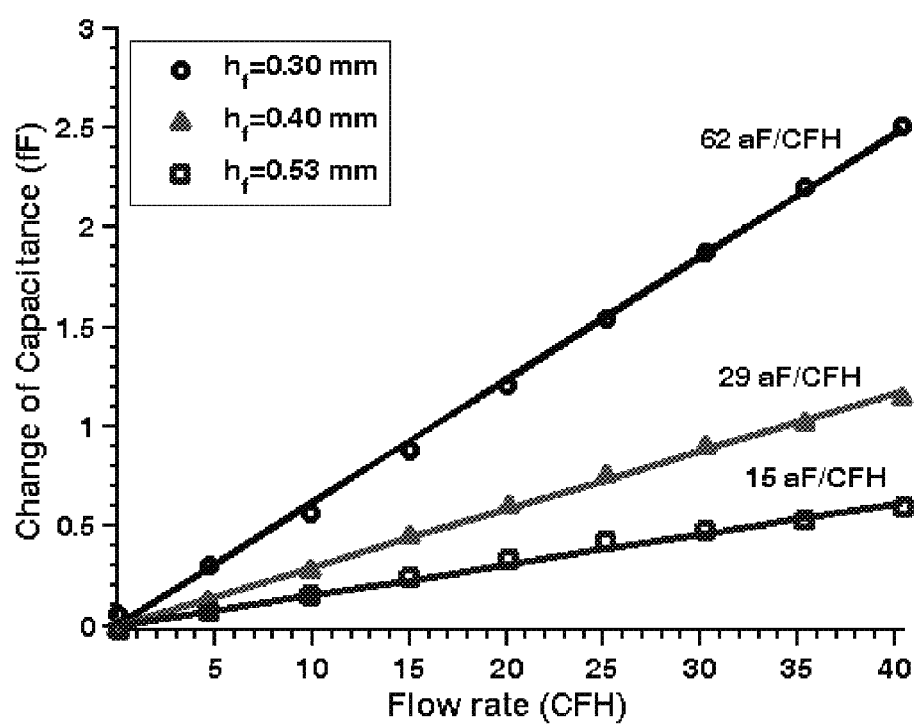
FIG. 11 shows measured change in capacitance vs. flow rate for all three channel heights. Best-fit lines are also shown.

FIG. 11 shows the average change in capacitance as a function of the flow rate for the three different channel heights. This average is computed for the 30 seconds of data at each stabilized flow rate. Since the data rate is 2.94 samples/sec, there are 90 measured values at each flow rate.

The standard deviation of the capacitance about the mean for the time domain data gives the noise density of the measurement. For all data measured in the 0.30 mm high duct, the standard deviation was 22.1 aF. A plot of the power spectral density of the capacitance noise shows that it is white noise. Hence, the noise density of the measurement is related to the standard deviation by $$P_x = \sqrt{\frac{2\sigma^2}{F_s}}, \quad (14)$$

where $P_x$ is the noise density in aF/√Hz, σ is the standard deviation in aF, and $F_s$=2.94 is the sample rate in samples/second. The noise density of the capacitance measurement is therefore 18.2 aF/√Hz at low frequencies (below 1.5 Hz). This is approximately double, but on the same order, as the typical noise of the unloaded AD7747 given on the datasheet, 9.0 aF/√Hz. The reduction in resolution could be due to loading effects on the AD7747, EMI, real fluctuations in flow rate, or using the sensitivity model given in equations (8) and (9), it is postulated that the change in capacitance can be related to the shear stress and pressure gradient by thermal-mechanical noise of the floating element.

$$\Delta C = S_2 \tau_{yx} + S_3 \frac{\partial P}{\partial x} \quad (15)$$

For each flow condition the pressure gradient and the shear stress are known, either from the flow rate according to equations (12) and (13), or from the measurement of pressure gradient. There are 24 non-zero flow conditions to evaluate and two constants to fit. This becomes a least squares problem; essentially one is fitting a plane to the data in shear stress-pressure gradient space. A linear least squares fit was performed to the 24 data points to determine the two sensitivities. It is emphasized that these sensitivities are for 8 groups of elements (128 individual elements) acting in parallel.

$S_2$=77.0 aF/Pa $S_3$=−15.8 aF/(Pa/mm) (16)

The norm of the residual is 56.6 aF, corresponding to 0.74 Pa of error. If, on the other hand, the pressure gradient sensitivity were neglected; that is, if $S_3$=0, then the best fit is S2=173 aF/Pa. For this case, the norm of the residual is 434 aF, corresponding to 2.5 Pa of error. A comparison of the measured vs. actual wall shear stress is given in FIG. 12 for the two cases. Correcting for pressure gradient sensitivity improves the accuracy of the measurement.

It is significant that correcting for pressure gradient sensitivity improves accuracy for these 3 flow cases, but the result has even greater importance than simply improving accuracy in laminar flow. If the sensor were to be used in a different flow regime, such as under a turbulent boundary layer with adverse or favorable pressure gradients, the substantial sensitivity to pressure gradient could cause inaccurate measurements of shear if neglected. For example, consider a flow measurement performed under a turbulent boundary layer with zero pressure gradient. If the actual wall shear were 10 Pa, but pressure gradient effects were neglected in the calibration, then the sensor would suggest that the wall shear was (S2/S3)(10 Pa)=4.4 Pa, a large error.

With the measured sensitivities in hand, it is now possible to go back to the electromechanical model developed in equations (8) and (9) to see what the effective surface area and effective volume of the element are. Keep in mind that there are 128 elements acting in parallel in the experiment, so the sensitivity will be 128 times that of equations (8) and (9). Using the measured dimensions from Table 1, and taking the modulus of electroplated Nickel to be E=205 GPa (Luo, A. Flewitt, S. Spearing, N. Fleck, W. Milne, Young's modulus of electroplated Ni thin film for MEMS applications, Mater Lett. 58 (2004) 2306-2309), the effective surface area of the element is $$\Delta x \Delta z = \frac{E d w^3}{128 \cdot N \varepsilon L^3} S_2 = 0.086 \text{ mm}^2, \quad (17)$$

which is nearly identical to the actual physical surface area of the shuttle, 0.085 mm². The effective volume of the element is $$\Delta x \Delta y \Delta z = \frac{-E d w^3}{128 \cdot N \varepsilon L^3} S_3 = 1.8 \cdot 10^{-2} \text{ mm}^3, \quad (18)$$

which is more than an order of magnitude larger than the physical volume of the shuttle, 7.5·10⁻⁴ mm³. On this basis it is concluded that the element shows nearly exactly the sensitivity to surface shear that would be predicted based solely on the physical surface area, but considerably more sensitivity to pressure gradient than would be predicted based on the physical volume. It seems likely that the increase in pressure gradient sensitivity is due to two factors: (1) the complexities of the flow around the microscale geometries of the beams, combs, and bumps leading to changes in pressure close to the element features (2) the topology of the package contributing to changes in the flow pattern at the scale of the entire chip, resulting in changes to the fluidic forces.

Two and three dimensional computational fluid dynamics results support the idea that flow around the edges of the element, the combs and the beams result in substantial increases in the pressure loading on the structure.

The unique array-based floating element shear stress sensor with surface bumps was developed with the ultimate goal of measuring local shear stress at small spatial scales. The chip includes 16 individually addressable groups in a 4 by 4 array with a spatial resolution of 2 mm. A capacitance to digital converter IC was used successfully to make digital differential capacitance measurements in laminar duct flows. Experiments conducted in three different height flow ducts allowed independent determination of the sensitivity to surface shear (77.0 aF/Pa) and pressure gradient (−15.8 aF/(Pa/mm)) for 8 groups (128 elements) acting in parallel. The noise density of the sensor is 0.24 Pa/A/Hz at low frequencies (below 1.5 Hz). Pressure gradient sensitivity is higher by approximately an order of magnitude than would be expected based solely on the physical volume of the element. For surface shear sensors of this type, it is useful to measure and include a correction for pressure gradient sensitivity in order to achieve accurate measurements of surface shear stress.

All publications and patents mentioned in the above specification are herein incorporated by reference as if expressly set forth herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

We claim:
1. A micromachined floating element array sensor, comprising:
a) a solid support comprising at least one array of a plurality of floating shear sensors wherein said shear sensors detect shear stress; and b) a controller configured to correct said shear stress for pressure gradient sensitivity by the steps of i) calibrating the pressure gradient sensitivity and shear sensitivity using two or more laminar flow cells with different slot heights at different flow rates; ii) determining the change in capacitance in each configuration; iii) performing a numerical fit of the measured data to the equation $$\Delta C = S_2 \tau_{yx} + S_3 \frac{\partial P}{\partial x}$$

in order to determine the sensitivity to shear, $S_2$ and the sensitivity to pressure gradient, $S_3$, where $\Delta C$ is the change in capacitance measured by the sensor, $\tau_{yx}$ is the shear stress, and $\partial P/\partial x$ is the pressure gradient.

2. The sensor of claim 1, wherein each of said shear sensors comprise a movable center shuttle, a plurality of sets of variable capacitors, and a series of folded beams.

3. The sensor of claim 1, wherein a top surface of said shear sensors comprise a plurality of surface bumps configured to increase said sensitivity of said shear sensor to pressure gradients.

4. The sensor of claim 1, wherein said sensors are in an at least 1 4×4 array.

5. The sensor of claim 1, wherein said sensors are in at least 2 4×4 arrays.

6. The sensor of claim 1, wherein said sensors are in at least 4 4×4 arrays.

7. The sensor of claim 1, wherein said array has a pitch of approximately 2 mm.

8. The sensor of claim 1, wherein said solid support is approximately 1 cm$^2$.

9. The sensor of claim 1, wherein said array comprises a plurality of electroplated layers of metal.

10. The sensor of claim 9, wherein said metal is one or more of copper or nickel.

11. The sensor of claim 9, wherein said array comprises at least 2 layers of electroplating.

12. The sensor of claim 1, wherein said shear sensors further comprise a capacitance to digital converter.

13. The device of claim 1, wherein said controller is further configured to calculate shear stress based on said correction of shear stress.

14. A system, comprising:
a) a micromachined floating element array sensor, comprising: a solid support comprising at least one array of a plurality of floating shear sensors wherein said shear sensors detect shear stress and are calibrated to determine the sensitivity of said sensors to pressure gradients; and
b) a controller configured to measure shear stress using said sensor and report said shear stress using said user interface, wherein said controller is further configured to correct said shear stress for pressure gradient sensitivity by the steps of i) calibrating the pressure gradient sensitivity and shear sensitivity using two or more laminar flow cells with different slot heights at different flow rates; ii) determining the change in capacitance in each configuration; iii) performing a numerical fit of the measured data to the equation $$\Delta C = S_2 \tau_{yx} + S_3 \frac{\partial P}{\partial x}$$

in order to determine the sensitivity to shear, $S_2$ and the sensitivity to pressure gradient, $S_3$ where $\Delta C$ is the change in capacitance measured by the sensor, $\tau_{yx}$ is the shear stress, and $\partial P/\partial x$ is the pressure gradient.

15. The system of claim 14, wherein said controller is further configured to calculate shear stress based on said correction of shear stress.

16. A method of detecting shear stress, comprising:
a) contacting a micromachined floating element array sensor, comprising: a solid support comprising at least one array of a plurality of floating shear sensors wherein said shear sensors detect shear stress and are calibrated to determine the sensitivity of said sensors to pressure gradients with a source of shear stress, and
b) measuring said shear stress, wherein said shear stress is corrected for pressure gradient sensitivity by the steps of i) calibrating the pressure gradient sensitivity and shear sensitivity using two or more laminar flow cells with different slot heights at different flow rates; ii) determining the change in capacitance in each configuration; iii) performing a numerical fit of the measured data to the equation $$\Delta C = S_2 \tau_{yx} + S_3 \frac{\partial P}{\partial x}$$

in order to determine the sensitivity to shear, $S_2$ and the sensitivity to pressure gradient, $S_3$ where $\Delta C$ is the change in capacitance measured by the sensor, $\tau_{yx}$ is the shear stress, and $\partial P/\partial x$ is the pressure gradient.

17. The method of claim 16 further comprising the step of measuring pressure gradient and correcting said shear stress value for said pressure gradient.

18. The method of claim 16, wherein said shear stress is under a turbulent boundary layer.

19. The method of claim 16, wherein said method further comprises the step of calculating shear stress based on said correction of shear stress.

* * * * *